United States Patent [19]

Dishman

[11] Patent Number: 4,924,173
[45] Date of Patent: May 8, 1990

[54] SHIELDED CAPACITANCE STANDARD

[75] Inventor: Michael R. Dishman, Raleigh, N.C.

[73] Assignee: Troxler Electronic Laboratories, Inc., Research Triangle Park, N.C.

[21] Appl. No.: 307,410

[22] Filed: Feb. 6, 1989

[51] Int. Cl.⁵ .................. G01N 27/02; G01R 27/26
[52] U.S. Cl. .................................. 324/690; 361/271
[58] Field of Search ............ 361/280, 271, 283, 286; 324/61 P, 61 R

[56] References Cited

U.S. PATENT DOCUMENTS

| | | | |
|---|---|---|---|
| 2,529,846 | 11/1950 | McBrayer | 324/61 R |
| 4,044,607 | 8/1977 | Deal . | |
| 4,147,976 | 4/1979 | Wang . | |
| 4,399,404 | 8/1983 | Resh . | |
| 4,736,156 | 4/1988 | Benson | 324/61 P |

OTHER PUBLICATIONS

In situ Measurement of Moisture in Soil and Similar Substances by Fringe Capacitance, by A. M. Thomas; J. Sci. Instrum., vol. 43, 1966, pp. 21-27.

A Frequency Shift Dielectric Soil Moisture Sensor, by Darold Wobschall; IEEE Transactions on Geoscience Electronics, vol. GE-16, No. 2, Apr. 1978, pp. 112-118.

Primary Examiner—Reinhard J. Eisenzopf
Assistant Examiner—Jose M. Jolis
Attorney, Agent, or Firm—Bell, Seltzer, Park & Gibson

[57] ABSTRACT

This invention relates to a capacitance standard for use with capacitance sensitive probes. The standard comprises a capacitor having a pair of spaced plates and a dielectric positioned therebetween. A shield attached to one of the plates forms an enclosure around the other plate to essentially shield the capacitor. The capacitance standard is therefore not affected by outside electrical fields and an accurate, reproducible capacitance value is provided.

10 Claims, 1 Drawing Sheet

SHIELDED CAPACITANCE STANDARD

FIELD OF THE INVENTION

The invention relates to a device for standardizing and calibrating capacitance moisture probes.

BACKGROUND OF THE INVENTION

One well known method for measuring moisture content of materials such as grain, soils and the like is by measuring the electrical capacitance of the material. The electrical capacitance of the material is directly related to the dielectric constant of the material. The dielectric constant of most soil materials and of dry grain is relatively low. The dielectric constant of water is significantly higher which substantially affects the overall dielectric constant of the materials depending on the concentration of the water in the materials. Therefore, a measurement of the dielectric constant or capacitance of a material can serve as an accurate measurement of the moisture content.

Capacitance sensitive probes are disclosed in U.S. Pat. Nos. 4,044,607 to Deal and 4,399,404 to Resh and in articles by A. M. Thomas, "In situ Measurement of Moisture in Soil and Similar Substances by Fringe Capacitance," *J. Sci. Instrum.*, Vol. 43, 1966, Pages 21–27 and D. Wobschall, "A Frequency Shift Dielectric Soil Moisture Sensor," *IEEE Transactions on Geoscience Electronics*, Vol. GE-16, No. 2, Apr. 1978, Pages 112-118. These probes generally comprise a pair of electrodes which are so arranged that the test material functions as a dielectric between the electrodes. The electrodes are in an electrical circuit which measures the capacitance by suitable means such as an oscillating LC network. Changes in capacitance cause a measurable frequency shift in the oscillating circuit and thus can provide an indication of the moisture content of the soil.

Capacitance moisture sensing probes however, are by necessity precision instruments. A slight change in the capacitance of soil may represent a substantial difference in moisture content. Therefore, capacitance moisture sensing probes must be highly sensitive to the capacitance and must be carefully calibrated to assure that the measured capacitance is accurately coordinated with the moisture content.

Because of variations in manufacturing tolerances, moisture sensing probes of the same design will not necessarily sense the same capacitance. Consequently, each capacitance sensing probe must be individually calibrated and as a practical matter the probe should be periodically checked to assure that the calibration has been maintained.

The most common method to calibrate a capacitance moisture probe, particularly a probe used to measure the moisture content of soil, is to prepare calibration standards with carefully measured portions of dry sand and water. The probe is inserted into each of the calibration standards and the frequency of the oscillating circuit is recorded. The frequencies then may be calibrated to correspond to the known moisture contents of each of the soil samples. The preparation of the samples is, however, a tedious and painstaking process which is prone to errors. Therefore, the probes tend to be recalibrated infrequently, if at all.

At least one device has been developed to provide a suitable substitute to simulate a particular moisture content. U.S. Pat. No. 4,147,976 to Wang discloses a calibrating device which is compatible with a grain moisture sensor. The grain moisture sensor has the appearance of a cup with an upright electrode centered therein. A second electrode is positioned in the wall of the cup and the capacitance is measured through the grain between the electrodes. The calibrating device comprises a pair of concentric dielectric tubes which form an annular space. The annular space is sealed at both ends and filled with metal, liquid or other materials which provide the device with a predetermined capacitance simulating grain having a particular moisture content. The calibrating device is then inserted into the cup and the capacitance is measured through the annular space. This type of device is, however, unsuitable for calibrating moisture probes of the type which are inserted into the soil because of the geometry of such probes. The electrodes of soil moisture probes are typically mounted on the periphery of a cylinder and are not suitably disposed to measure capacitance through an annular space. Also, outside electrical fields have a tendency to affect the measurement of capacitance by the moisture probe. This problem is not seriously encountered while down in the soil, but out in the open it becomes a greater concern. The Wang device provides no measure of protection against outside electrical fields.

Accordingly, it is an object of the present invention to provide a capacitance standard for use to calibrate capacitance moisture probes which avoids the disadvantages of the prior art as noted above.

It is a more particular object of the present invention to provide a capacitance standard for use to calibrate capacitance moisture probes which provides an inexpensive reliable capacitance measurement and which is not affected by outside electrical fields.

SUMMARY OF THE INVENTION

The above and other objects of the invention have been achieved in the present invention by the provision of a shielded capacitance standard comprising a capacitor having respective plates and a dielectric cooperating to define a capacitance of fixed value. The capacitance standard is provided with means for connecting electrodes of a capacitance sensitive probe to the respective plates of the capacitor so that the probe will measure the fixed value capacitance. The shielded capacitance standard further has a shield which cooperates with the capacitor to shield the capacitor and the probe from external fields so that the measured capacitance is accurate and reproducible, facilitating the calibration of capacitance sensitive probes.

BRIEF DESCRIPTION OF THE DRAWINGS

Some of the features and advantages have been stated and others will become apparent as the description proceeds when taken in conjunction with the accompanying drawings, in which.

DETAILED DESCRIPTION OF THE PREFERRED EMBODIMENT

Figure 1:
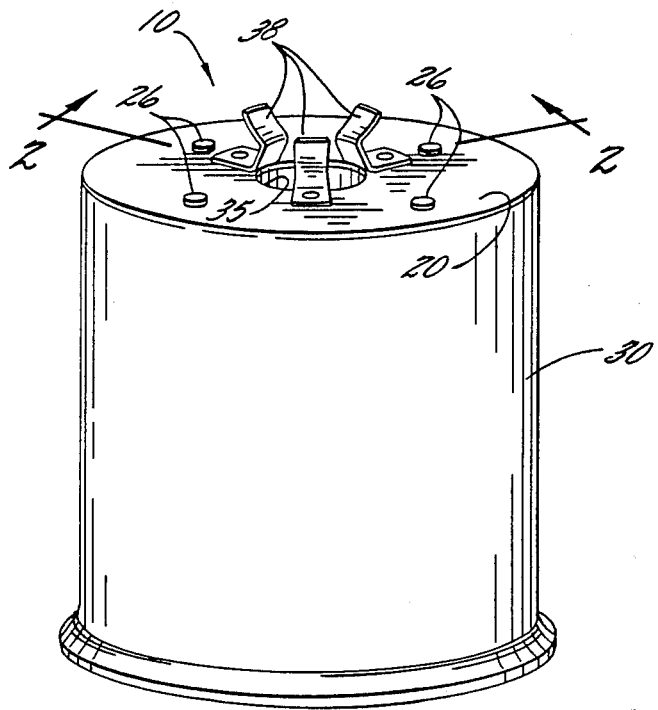
FIG. 1 is a perspective view of the shielded capacitance standard which embodies the features of the present invention.
Figure 2:
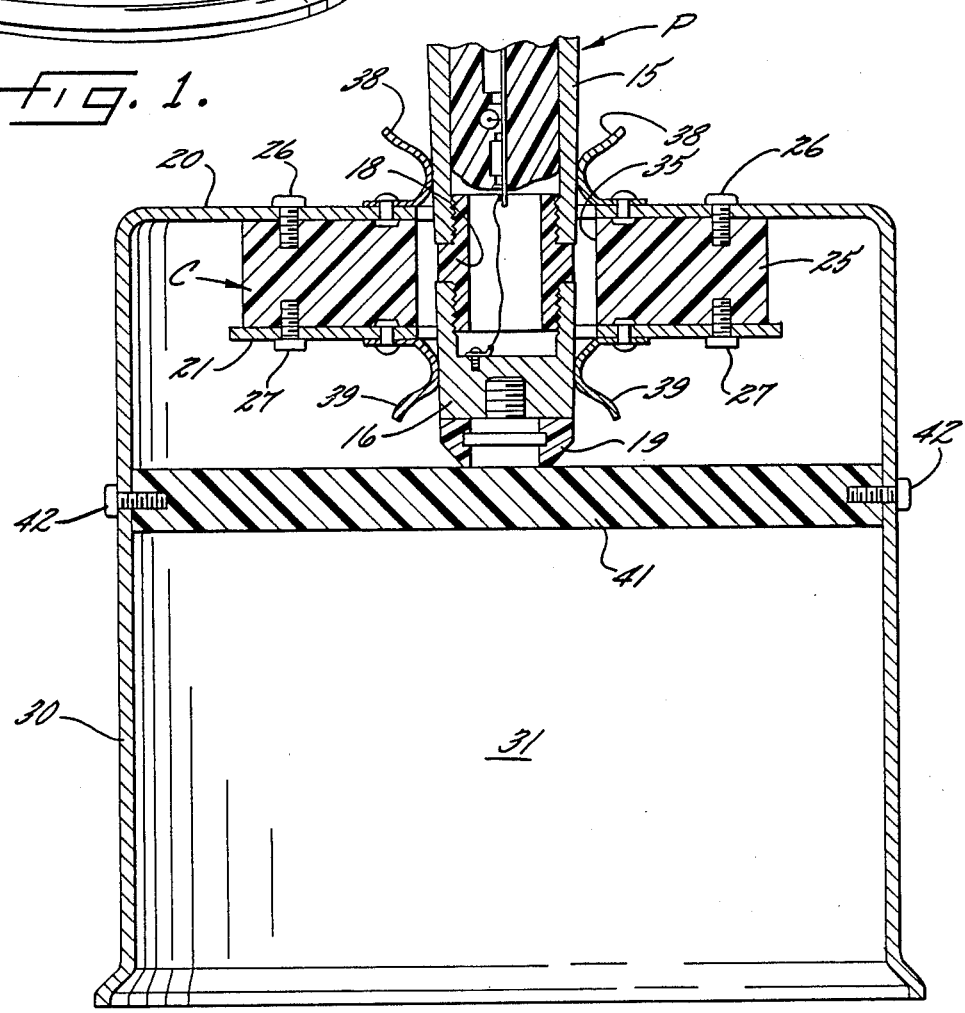
FIG. 2 is an enlarged cross-sectional view of the shielded capacitance standard taken substantially along the line 2—2 in FIG. 1.

Referring now more particularly to the drawings, FIGS. 1 and 2 illustrate the preferred embodiment of a shielded capacitance standard, generally indicated by the numeral 10. The shielded capacitance standard 10 is used in conjunction with capacitive sensitive probes for facilitating calibration thereof. In the illustrated embodiment (FIG. 2), the capacitance sensitive probe P is generally cylindrical in shape with electrodes spaced apart by a dielectric. The probe P illustrated herein is described in greater detail in copending U.S. patent application No. 07/268,935 filed Nov. 8, 1988, the disclosure of which is incorporated herein by reference. Briefly, probe P comprises first and second electrodes 15 and 16 spaced apart by a dielectric spacer 18. A dielectric tip 19 is attached to the electrode 16 so as to space the electrode from the end of the probe P. The electrodes are electrically connected to an electronic circuit (not shown) for measuring the frequency shift in an LC circuit. The probe P is primarily intended for measuring the ground moisture content of soil and to obtain optimum contact with the soil the probe has a slight taper which will be accommodated by the capacitance standard as explained below.

The preferred embodiment of the capacitance standard includes a capacitor C comprising a metallic first plate 20 and a generally parallel metallic second inner plate 21 spaced apart by a dielectric 25. The dielectric 25 is attached to the first plate 20 in an overlying manner by conventional means such as screws 26. The second plate 21 is similarly attached to the dielectric 25 in an overlying manner by screws 27. The capacitance of the capacitor C is a fixed value which is the result of a combination of the size and shape of the plates, the thickness of the dielectric, the dielectric constant of material or materials used in the dielectric and other factors known to persons having ordinary skill in the art. In the preferred embodiment, the plates are made of stainless steel, aluminum or other corrosion resistent metal. The dielectric is formed from a block of a hydrophobic polymer material having a relatively high dielectric constant. Since the polymer material is hydrophobic, having little or no affinity for water, its dielectric properties do not fluctuate with fluctuations in ambient humidity. A preferred polymer material having these properties is polyethylene, or a polyvinylidene fluoride material. These materials are relatively rigid and durable so as to maintain a constant spacing between the plates 20 and 21.

The shielded capacitance standard 10 comprises a metallic enclosure having a top portion 20 and a side wall portion 30 defining an enclosed shielded space 31. The top portion 20 of the enclosure also serves as the first plate of the capacitor. The dielectric 25 and second plate 21 are disposed within the enclosed shielded space 31 so that the capacitor is shielded from outside electrical fields which might affect the measurement of the capacitance value of the capacitor. In the preferred embodiment the upper portion 20 of the metallic enclosure and the enclosing wall 30 are integrally formed and define a generally cylindrical enclosure.

As illustrated, a hole 35 is located in the central portion of the first plate 20 and extends through the dielectric 25 and the inner plate 21 for receiving the probe P down into the shielded space 31. Thus, when a probe P is inserted into the hole as shown in FIG. 2, the electrodes 15, 16 of the probe are located interiorly of the shielded enclosure and are therefore shielded from outside electrical fields as is the capacitor. Contacts 38 are mounted on the upper surface of plate 20 and are disposed around the hole 35 for providing electrical contact between the electrode 15 and the plate 20. Similarly, contacts 39 are mounted on the exposed under surface of inner plate 21 and ar arranged around the hole 35 for contacting the electrode 16 of probe P. The contacts have a shape generally similar to the shape of a "C" and are made of spring steel or other flexible conductive material to be spring biased toward the hole. The contacts therefore bend and conform to the dimension of the probe and accommodate variations in the diameters of the probes as well as the taper of the probe P. The contacts are fixed to the plates by conventional means such as rivets. In this arrangement, as clearly shown in FIG. 2, the capacitor C bridges across the electrodes 15 and 16 so that a capacitance measurement taken by probe P is that of the capacitor.

To provide proper alignment of the electrodes with the contacts, a stop 41 is mounted within the shielded enclosure extending beneath the hole at an appropriate distance to limit the depth the probe may be inserted into the hole 35. The stop is secured to the wall 30 by suitable fastener means, such as bolts 42. In the preferred embodiment, the stop 41 is formed of a nonconductive dielectric material so as to be electrically insulated from the probe, even if the probe should be electrically conductive at the tip. The dielectric material is preferably a polyethylene or polyvinylidene fluoride material, although other suitable materials may be used.

In use, several capacitance standards are provided having a range of capacitance values covering the range of moisture contents which are to be measured. The probes may be calibrated over the range of moisture contents by measuring the capacitance of each standard and establishing therefrom appropriate calibration curves or equations relating the capacitance reading of the probe to a moisture content reading.

The foregoing description is to be considered illustrative rather than restrictive of the invention, and those modifications which come within the meaning and range of equivalence of the claims are to be included therein.

That which is claimed:

1. A shielded capacitance standard for use with a capacitance sensitive probe having electrodes mounted for sensing a capacitance adjacent thereto, said standard comprising:

capacitor means having respective plates and a dielectric cooperating to define a capacitance of fixed value;

means cooperating with said capacitor means for connecting the electrodes of the probe to the respective plates of the capacitor so that the probe will measure said fixed value capacitance; and shield means for shielding both the capacitor means and the probe from external electrical fields and comprising a generally cylindrical metallic enclosing wall adjoining and extending from one of said plates of said capacitor means to define a shielded space wherein said capacitor means is generally disposed within said shielded space thereby providing an accurate and reproducible standard for facilitating the calibration of capacitance sensitive probes.

2. A shielded capacitance standard characterized by having a capacitance of fixed value and which is not substantially affected by outside electrical fields for use with a capacitance sensitive probe having a plurality of electrodes for sensing the capacitance of materials adjacent the electrodes, the standard comprising:

a metallic enclosure having a generally circular top portion and cylindrical side wall portions extending downwardly from said top portion;

a metallic inner plate located within said metallic enclosure;

a dielectric located within said metallic enclosure and sandwiched between said metallic and the inner surface of said top portion;

said top portion of said metallic enclosure and said inner plate cooperating with said dielectric to form a shielded capacitor having a capacitance of fixed value;

a hole extending through said top portion, said dielectric, and said inner plate for receiving the capacitance sensitive probe;

a plurality of spring biased electrical contacts attached to said top portion and said inner plate in positions adjacent said hole for electrically connecting said top portion and said inner plate to the respective electrodes of the probe; and dielectric stop means attached to said metallic enclosure to limit the depth a probe may be inserted into said hole so that the electrodes of the probe are aligned with said electrical contacts.

3. The shielded capacitance standard according to claim 1 wherein said capacitor means comprises a pair of electrically conductive plates and a solid dielectric positioned therebetween.

4. The shielded capacitance standard according to claim 3 wherein said means for connecting the electrodes of the probe to the respective plates includes electrical contacts attached to each said plate and positioned for contacting the electrodes of the probe.

5. A shielded capacitance standard for use with a capacitance sensitive probe having electrodes mounted for sensing a capacitance adjacent thereto, said standard comprising:

capacitor means comprising a pair of electrically conductive plates and a solid dielectric positioned therebetween to define a capacitance of fixed value;

means cooperating with said capacitor means for connecting the electrodes of the probe to the respective plates of the capacitor so that the probe will measure said fixed value capacitance; and shield means cooperating with said capacitor means and with said probe for shielding both the capacitor means and the probe from external electrical fields, thereby providing an accurate and reproducible standard for facilitating the calibration of capacitance sensitive probes;

wherein said capacitor means includes a hole extending through said pair of plates and said dielectric for receiving the capacitance sensitive probe, and wherein said means for connecting the electrodes of the probe to the respective plates includes electrical contacts carried by the respective plates and positioned adjacent said hole for contacting the surface of a probe inserted in the hole.

6. The shielded capacitance standard according to claim 5 wherein said electrical contacts are spring biased toward the hole where the probe is inserted.

7. The shielded capacitance standard according to claim 5 further including a dielectric stop positioned to limit the depth a probe may be inserted into said hole.

8. A shielded capacitance standard for use with a capacitance sensitive probe having electrodes mounted for sensing a capacitance adjacent thereto, said standard comprising:

capacitor means comprising a pair of metallic plates and a dielectric cooperating to define a capacitance of fixed value;

means cooperating with said capacitor means for connecting the electrodes of the probe to the respective plates of the capacitor so that the probe will measure said fixed value capacitance; and shield means cooperating with said capacitor means and with said probe for shielding both the capacitor means and the probe from external electrical fields, said shield means comprising; a metallic enclosure adjoining and extending from one of said metallic plates such that the one plate and said shield are formed as an integral unit, said integral unit defining a shielded space, with said dielectric and the other plate being positioned within the shielded space and including a hole formed in said capacitor means for receiving the probe so that at least a portion of the probe is received in the shielded space and outside electrical fields are shielded from the capacitor and the probe.

9. A shielded capacitance standard for use with a capacitance sensitive probe having a plurality of electrodes for sensing the capacitance of materials adjacent the electrodes, the standard comprising:

a metallic enclosure having a top portion and peripheral side wall portions extending downwardly from said top portion to define an enclosed shielded space;

a metallic inner plate located within said metallic enclosure;

a dielectric located within said metallic enclosure and sandwiched between said metallic inner plate and the inner surface of said top portion;

said top portion of said metallic enclosure and said inner plate cooperating with said dielectric to form a shielded capacitor having a capacitance of fixed value; and a hole extending through said top portion, said dielectric and said inner plate for receiving the capacitance sensitive probe.

10. The shielded capacitance standard according to claim 9 further including a plurality of electrical contacts attached to said top portion and said inner plate for providing electrical contact between said top portion and said inner plate and respective electrodes of the probe.

* * * * *